(12) United States Patent
Traub (10) Patent No.: US 8,555,892 B2
(45) Date of Patent: Oct. 15, 2013

(54) MAYO STAND DRAPE WITH SELF-DISPOSING FEATURE

(75) Inventor: Craig D. Traub, Andover, MA (US)

(73) Assignee: OBP Corporation, Lawrence, MA (US)

( * ) Notice: Subject to any disclaimer, the term of this patent is extended or adjusted under 35 U.S.C. 154(b) by 28 days.

(21) Appl. No.: 12/891,068

(22) Filed: Sep. 27, 2010

(65) Prior Publication Data

US 2011/0073507 A1     Mar. 31, 2011

Related U.S. Application Data

(60) Provisional application No. 61/246,417, filed on Sep. 28, 2009.

(51) Int. Cl.
*A61B 19/00*     (2006.01)

(52) U.S. Cl.
USPC ............................ 128/849; 128/852; 206/440

(58) Field of Classification Search
USPC ................................................. 128/849–855
See application file for complete search history.

(56) References Cited

U.S. PATENT DOCUMENTS

| | | | | |
|---|---|---|---|---|
| 5,170,804 A | * | 12/1992 | Glassman | 128/849 |
| 6,255,627 B1 | * | 7/2001 | Faries et al. | 219/430 |
| 6,497,233 B1 | * | 12/2002 | DeAngelis | 128/849 |
| 8,042,688 B2 | * | 10/2011 | Parks et al. | 206/438 |

* cited by examiner

*Primary Examiner* — Patricia Bianco
*Assistant Examiner* — Camtu Nguyen
(74) *Attorney, Agent, or Firm* — CKC & Partners Co., Ltd.

(57) ABSTRACT

In certain embodiments, the present invention provides a protective sterile drape for a Mayo surgical tray stand that has a self-disposing feature, the ability at the end of a surgical procedure to draw the drape around the disposable instrument tray, disposable instruments and disposable surgical waste and secure the drape and its contents with a provided closure device to produce a closed container suitable for disposal. In preferred embodiments, the drape further includes a disposable instrument tray, consumable supplies and disposable instruments that are selected for a specific procedure.

18 Claims, 7 Drawing Sheets

MAYO STAND DRAPE WITH SELF-DISPOSING FEATURE

RELATED APPLICATION

This application claims benefit of U.S. Provisional Patent Application 61/246,417, filed Sep. 28, 2009, the entire contents of which are incorporated by reference for all purposes.

FIELD OF THE INVENTION

The present invention relates generally to a protective sterile cover for a surgical tray stand used in a medical facility. The present invention also relates to disposable drapes for a Mayo surgical tray stand that are packaged with a tray, consumable supplies and single-use instruments, which provides for easy collection and disposal of drape, tray, waste, and single-use instruments.

BACKGROUND OF THE INVENTION

A Mayo surgical tray stand is a movable stand having a horizontal, generally rectangular, frame within which a tray for holding surgical instruments may be placed, a vertical support member connecting the horizontal frame to a base, and a base having base extensions and at least one pair of wheels or casters to provide ease of maneuverability in an operating room or other surgical area. When viewed from the side, the shape of the Mayo surgical tray stand approximates an open "C," a shape that allows the horizontal tray to be fitted above the foot end of a patient on an examination or surgical table to make the tray and instruments readily accessible to a nurse who hands instruments from the tray to the operating surgeon. When the operating surgeon is finished using a particular instrument, the instrument is given back to the assisting nurse who then replaces the instrument back on the tray for later use. Accordingly, the primary purpose of a Mayo surgical tray stand and drape is to provide a sterilized tray for the orderly placement thereon of surgical instruments at a location that is conveniently located to allow efficient handling of the different surgical instruments as needed by the surgeon throughout the surgery.

Mayo surgical tray stands are also frequently used in doctors' offices for office-based procedures. In office applications, the Mayo surgical tray stand is not placed over the surgical table, but placed beside the doctor. In office-based procedures it is important that the equipment used in the procedure be quickly accessible on the Mayo stand, and that post-procedure cleanup is quick and easy.

Figure 1:
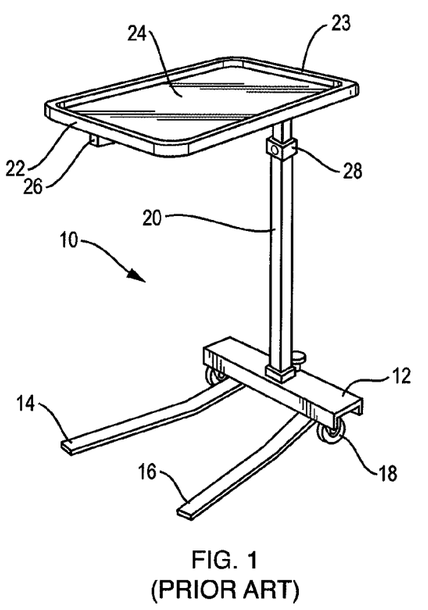
FIG. 1 is a perspective view of an embodiment of a prior art Mayo surgical tray stand 10.

FIG. 1 is a perspective view of a prior art Mayo surgical tray stand 10, with a generally rectangular support ring 22, a vertical support member 20 and a base 12. The base 12 includes a first base extension 14, a second base extension 16 and a pair of casters 18. The horizontal generally rectangular support ring 22 is adapted to receive a surgical tray 24 that has a formed tray edge 23 adapted to fit on top of the generally rectangular support ring 22. In some embodiments, the generally rectangular support ring 22 is strengthened by an auxiliary support arm 26. Generally, the length of the vertical support member 20 can be changed to adjust the generally rectangular support ring 22 to a convenient height. Accordingly, an adjustment means 28 is often provided.

Figure 2:
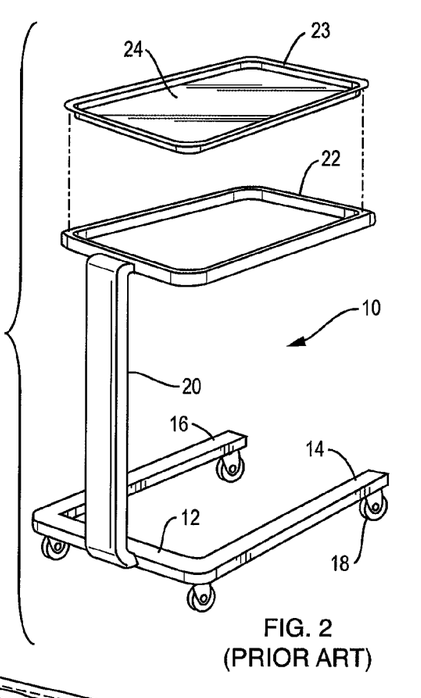
FIG. 2 is a perspective view of another embodiment of a prior art Mayo surgical tray stand 10.

FIG. 2 is a perspective view of another prior art Mayo surgical tray stand 10, with a generally rectangular support ring 22, a vertical support member 20 and a base 12. The base 12 includes a first base extension 14, a second base extension 16 and two pairs of casters 18. The tray 24 with edge 23 is shown above the rectangular support ring 22.

Figure 3:
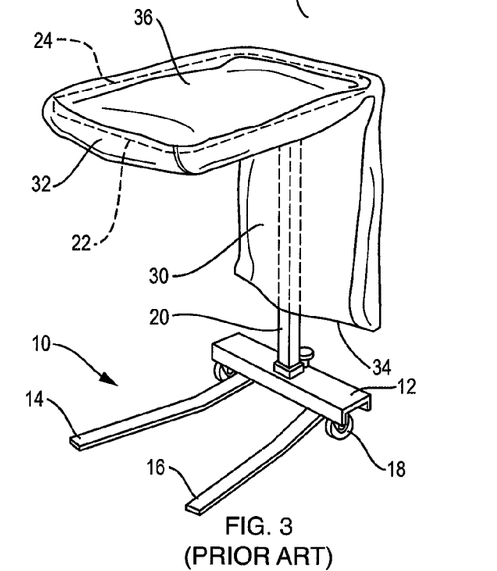
FIG. 3 is a perspective view of an embodiment of a prior art Mayo surgical tray stand cover 30 in place on a Mayo stand 10 of FIG. 1.

The basic prior art surgical drape for the Mayo surgical tray stand is a flattened rectangular bag, much like an elongated pillow case, that fits over the horizontal tray portion of the Mayo surgical tray stand and the vertical support member. FIG. 3 is a perspective view of such a prior art Mayo surgical tray stand cover 30 installed on a Mayo surgical tray stand 10. The Mayo surgical tray stand cover 30 has a closed end 32 and an open end 34. The Mayo surgical tray stand 10 has a generally rectangular support ring 22, a vertical support member 20 and a base 12. The base 12 includes a first base extension 14, a second base extension 16 and a pair of casters 18. The tray 24 is shown placed on the rectangular support ring 22, and covered by a region 36 of the Mayo surgical tray stand cover 30 that may be made to have "non-skid" properties. Mayo stand covers of this design have been disclosed in U.S. Pat. No. 3,335,719 (Boucher), U.S. Pat. No. 3,738,405 (Ericson), U.S. Pat. No. 3,747,655 (Hadtke), U.S. Pat. No. 5,379,703 (Marshall), U.S. Pat. No. 5,411,036 (Wilkes), U.S. Pat. No. 5,871,015 (Lofgren et al.), and U.S. Pat. Publication No. 2005/0229937 (Salvaggio et al.).

Figure 4A:
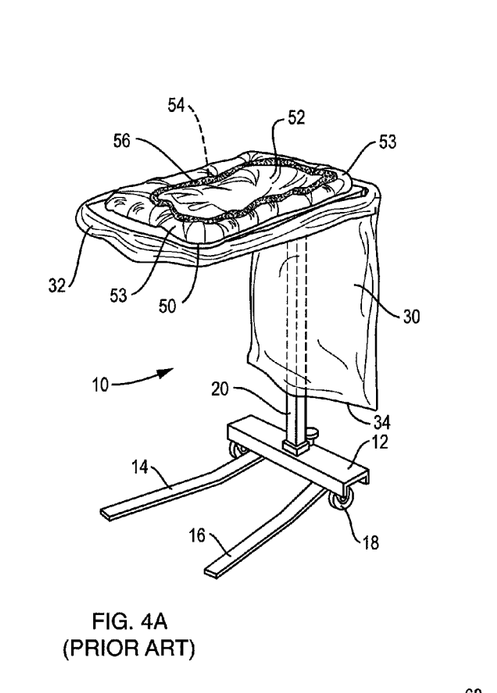
FIG. 4A is a perspective view of an embodiment of a prior art Mayo surgical tray stand cover 30 in place on a Mayo surgical tray stand 10 of FIG. 1 having a secondary cover 50 in addition to the Mayo surgical tray stand cover 30.
Figure 4B:
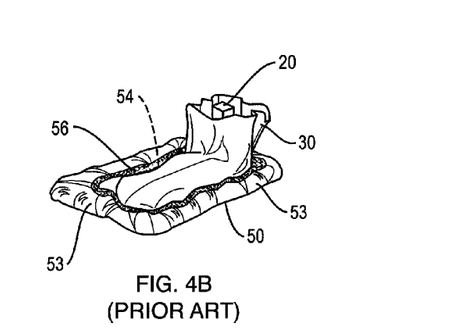
FIG. 4B is a perspective view of the underside of the Mayo surgical tray stand showing the secondary cover 50 deployed over the Mayo surgical tray stand cover 30.

Modifications of the basic prior art Mayo surgical tray stand cover have added secondary drapes to the tray region of the flattened rectangular bag. FIG. 4A and FIG. 4B are perspective views of a prior art Mayo surgical tray stand cover 30 with an additional secondary tray stand cover 50, in position on the prior art Mayo surgical tray stand 10. FIG. 4A is a perspective view of a prior art Mayo surgical tray stand cover 30 having a closed end 32 and an open end 34 that covers the horizontal support ring and tray portion of the Mayo surgical tray stand, and which extends to cover a substantial portion of the vertical member 20. Also shown are the base 12, first base extension 14, second base extension 16 and casters 18 of the Mayo surgical tray stand 10. A secondary tray stand cover 50 is added to the prior art Mayo surgical tray stand cover 30, the secondary tray stand cover 50 having a center 52, a side skirt 53, and a tensioning structure 54 enclosed within the hem 56 of the secondary tray cover. FIG. 4B shows a perspective view of the underside of the horizontal generally rectangular support ring 20 and tray portion of the Mayo surgical tray stand showing a portion of the vertical support member 20. The basic Mayo surgical tray stand cover 30 and the secondary tray stand cover 50 are in place, showing that the side skirt 53 has been placed down and under the horizontal generally rectangular support ring 22 and tray portion of the Mayo surgical tray stand and drawn by the tensioning structure 54 to partially cover the closed end of the Mayo surgical tray stand cover 30. Mayo surgical tray stand covers of this design are disclosed in U.S. Pat. No. 7,104,201 (Comeaux et al.).

Figure 5:
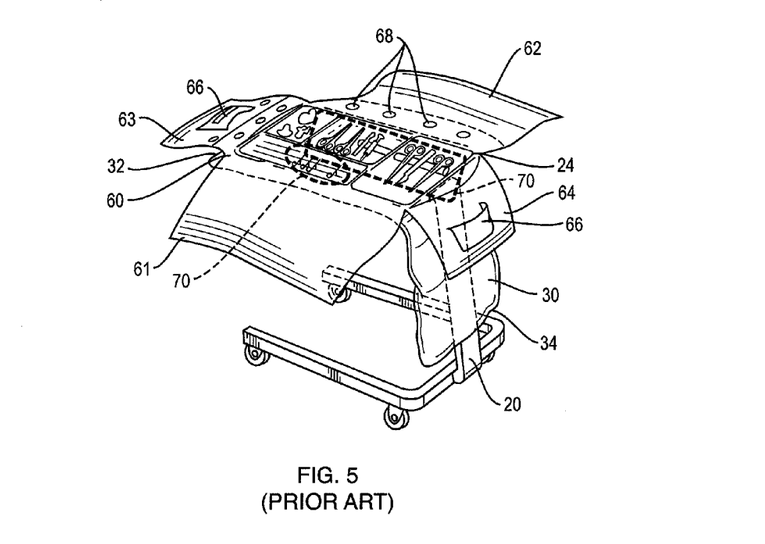
FIG. 5 is a perspective view of another embodiment of a prior art Mayo surgical tray stand cover in place on a Mayo surgical tray stand 10 of FIG. 2 having a secondary cover 60 in addition to the Mayo surgical tray stand cover 30.

Another modification of the basic prior art Mayo surgical tray stand cover adds a secondary drape with flaps and pockets to the tray region of the flattened rectangular bag. FIG. 5 shows another prior art Mayo surgical tray stand cover 30 in which a different embodiment of a secondary cover 60 is added to the prior art Mayo stand cover 30 shown in use on the prior art Mayo surgical tray stand 10. Secondary cover 60 has four side flaps 61, 62, 63 and 64. The secondary cover 60 is placed on top and oriented to the closed end 32 of the Mayo surgical tray stand cover 30. The secondary cover 60 has pockets 66, holes for placement of instruments 68 and groups of instruments 70 placed on the tray 24. Mayo surgical tray stand covers of this design are disclosed in U.S. Pat. No. 5,170,804 (Glassman).

SUMMARY OF THE INVENTION

In certain embodiments, the present invention provides a protective sterile drape for a Mayo surgical tray stand with a self-disposing feature, the ability to draw the drape around the disposable instrument tray, disposable instruments and disposable surgical waste and secure the drape and its contents with a provided closure device to produce a closed container suitable for disposal at the end of a surgical procedure. In preferred embodiments, the drape further includes a disposable instrument tray, consumable supplies and disposable instruments that are selected for a specific procedure.

In certain embodiments, the Mayo surgical tray stand drape comprises a bottom panel having an inner surface and an outer surface, the bottom panel having a length and width slightly larger than a length and width of a Mayo surgical tray, at least one side having an inner surface and an outer surface, the side attached to the bottom panel and disposed substantially perpendicular to the bottom panel, wherein the bottom panel and the attached side define a partially enclosed space having an opening opposite to the bottom panel, and at least one closure device. Typically, the drape is made of a sterilizable flexible material having a substantially liquid-impermeable layer. In preferred embodiments, the drape has four sides, each side being attached at one corresponding edge to an edge of the bottom panel to form a basal junction, and each slide attached to the adjacent sides on the edges adjacent to the basal junction to form four lateral junctions. In other embodiments, the bottom panel and the side are continuous. In preferred embodiments, the drape includes a surgical instrument tray, consumable supplies and instruments, and more preferably, the surgical instrument tray, consumable supplies and instruments are disposable. In some preferred embodiments, the surgical instrument tray is affixed to the inner surface of the bottom panel. Preferably, the drape includes at least one pocket affixed to the inner surface of at least one side. Typically, the drape includes at least one waste receptacle affixed to the inner surface of at least one side. In certain embodiments, the closure device is a draw tape, a tie cord, a self-adhesive tie, or a clamping closure device.

In further embodiments, the drape comprises a bottom panel and four side panels constructed of a sterilizable flexible material having a substantially liquid-impermeable layer, wherein each side panel is attached at one corresponding edge to an edge of the bottom panel to form a basal junction, and attached to the adjacent side panels on the edges adjacent to the basal junction to form four lateral junctions, and at least one closure device.

In other embodiments, the drape comprises an elongated enclosure made of a sterilizable flexible material having a substantially liquid-impermeable layer, the elongated enclosure having an open end and a closed end formed by a panel dimensioned to be about size and shape of a Mayo instrument tray and perpendicular to the longitudinal axis of the elongated enclosure, the distance between the hem of the open end and the basal junction of the closed end being less than the distance from the support ring of a Mayo stand to the floor, and a closure device.

DESCRIPTION OF PREFERRED EMBODIMENTS

The increasing use of office-based procedures has created needs that are not met by the prior art Mayo surgical tray stand covers. For example, a disadvantage of the prior art Mayo surgical tray stand cover is that the elongated tube style does not contain a pre-sterilized tray or instruments that are suitable for a given procedure. While some prior art modified Mayo stand covers may provide pockets for interim instrument storage during a procedure, such covers do not aid in quick and efficient clean-up after a procedure.

In preferred embodiments, the Mayo surgical tray stand drape of the present invention permits office-based surgical procedures to be performed more efficiently due to the ease of set-up, the ease of use, and the ease of cleanup. In office-based procedures, the surgeon is often not assisted by a nurse. Preferred embodiments of the present Mayo surgical tray stand drape provide pockets for interim storage of instruments and a self-disposing feature that provides a simple, convenient clean-up. When such embodiments of a Mayo surgical tray stand drape are used in office-based procedures, nursing assistance may not be required.

The embodiments of the Mayo surgical tray stand drape of the present invention are made from disposable sterilizable flexible drape material that has a substantially liquid-impermeable layer. Typically, the material includes a layer of non-woven fabric that is capable of absorbing liquid, and a layer of plastic film that is liquid-resistant or substantially liquid-impermeable. See, e.g., U.S. Pat. No. 4,535,481 (Ruth-Larsen et al.), U.S. Pat. No. 5,151,314 (Brown), and U.S. Pat. No. 5,743,273 (Newman).

Figure 6A:
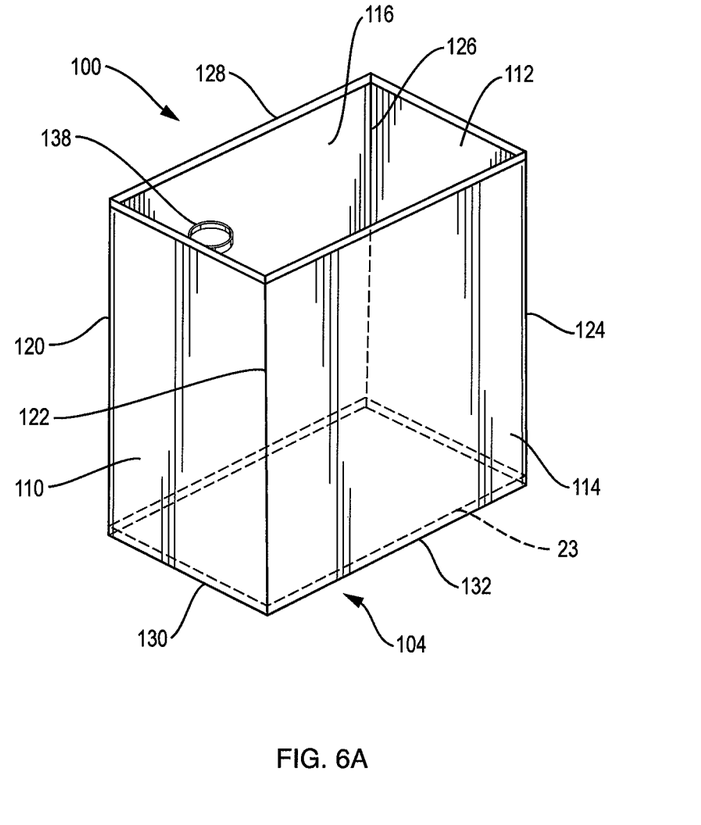
FIG. 6A is a perspective view of an embodiment of an open Mayo surgical tray stand drape 100 with a self-disposing feature.

FIG. 6 is a perspective view of an embodiment of the Mayo surgical tray stand drape 100 of the present invention, having a bottom panel 104, sides extending vertically from respective junctions with the bottom panel 104, consisting of a first short side 110, a second short side 112, a first long side 114 and a second long side 116, each side and the bottom panel 104 having an inner surface and an outer surface, wherein each inner surface is adjacent to the partially enclosed space defined by the bottom panel 104 and the sides 110, 112, 114, and 116. The dimensions of the bottom panel 104 are chosen to enclose a disposable Mayo surgical instrument tray, indicated by the tray edge 23. The sides 110, 112, 114, and 116 are joined to the bottom panel 104 at the respective basal junctions 130, 132, 134, 136. The lateral edges of the adjacent sides are joined together at lateral junctions 120, 122, 124 and 126. The edges of the joined sides opposite the basal junctions are joined to form a hem 128. A closure device is provided, and in preferred embodiments, the closure device is a draw tape 138 contained within the hem 128.

Figure 6B:
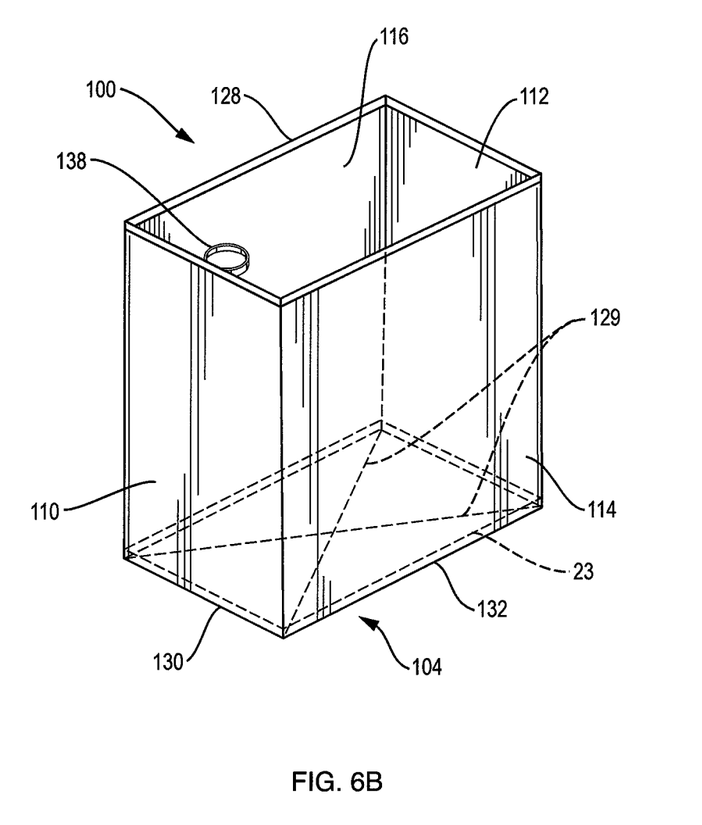
FIG. 6B is a perspective view of another embodiment of an open Mayo surgical tray stand drape 100 with a self-disposing feature.

The basal junctions and lateral junctions may be joined by adhesive, welding, stitching, or may be continuous. FIG. 6B illustrates another embodiment in which the Mayo surgical tray stand drape 100 is formed from a tube of disposable sterilizable flexible drape material so that the sides 110, 112, 114, and 116 are continuous, without lateral junctions. The bottom panel 104 in some such embodiments may be formed from segments that are continuous with the sides, the segments being joined at seams 129. The seams 129 may be joined by adhesive, welding, or stitching. In further embodiments, the Mayo stand drape 100 is formed from a tube of material so that the sides 110, 112, 114, and 116 are continuous and the bottom panel 104 is a single piece joined to the sides at continuous basal junctions. Methods of forming flat-bottomed containers, e.g., U.S. Pat. No. 5,265,961 (Boyd) and draw-tape closure devices, e.g., U.S. Pat. No. 4,558,463 (Boyd) and U.S. Pat. No. 5,265,961 (Boyd) are known in the art.

Figure 7:
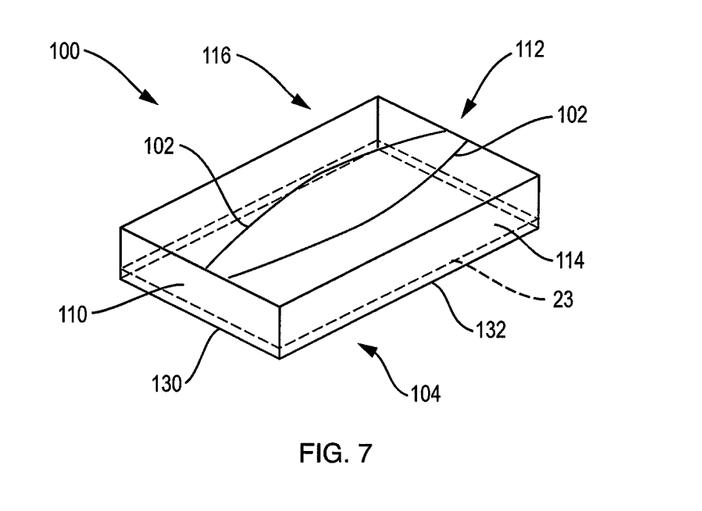
FIG. 7 is a perspective view of an embodiment of the folded Mayo surgical tray stand drape 100 of the present invention.

FIG. 7 is a perspective view of the packaged sterilized Mayo surgical tray stand drape 100 with sides 110, 112, 114, and 116 gathered into folds 102 on the side of the package opposite the bottom panel 104. The edge 23 of the enclosed disposable Mayo instrument tray is indicated.

In use, the package sterilized Mayo surgical tray stand drape 100 is placed on a standard Mayo surgical tray stand, the package opened, and the hem of the Mayo surgical tray stand drape pulled down over the Mayo surgical tray stand, exposing the enclosed tray and its contents, and turning the Mayo surgical tray stand drape inside out, i.e., everting the Mayo surgical tray stand drape.

Figure 8A:
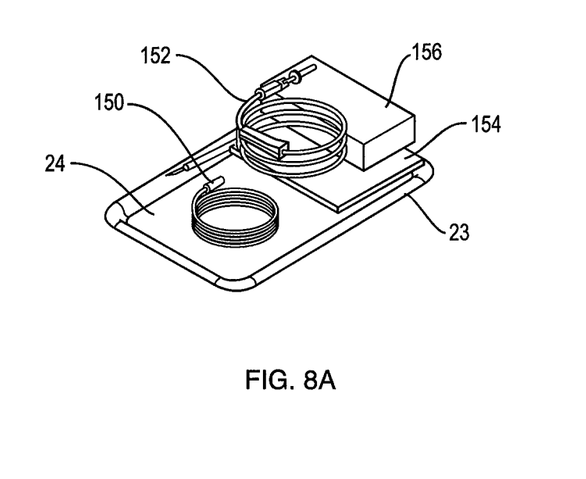
FIGS. 8A and 8B are perspective views of an embodiment of a disposable Mayo surgical instrument tray 24 with contents (FIG. 8A) and an embodiment of the present Mayo surgical tray stand drape 100 (FIG. 8B) showing the Mayo surgical tray stand drape 100 everted for use.
Figure 8B:
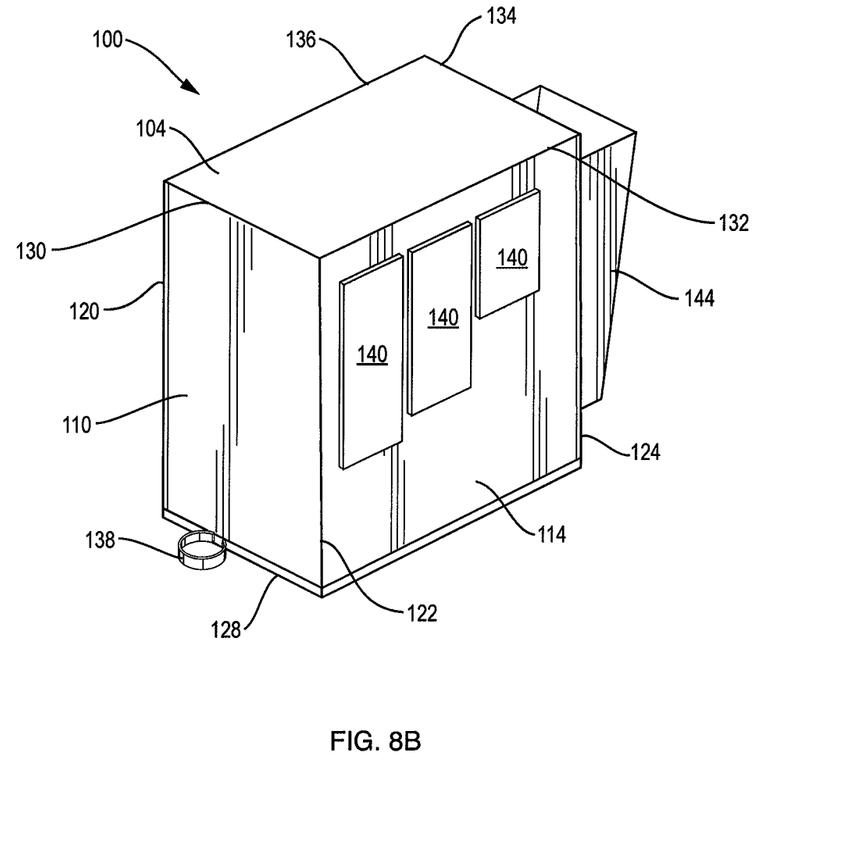

FIG. 8A and FIG. 8B are perspective views of the enclosed tray and contents (FIG. 8A) vertically displaced for illustration purposes from the everted Mayo surgical tray stand drape 100 (FIG. 8B). FIG. 8A illustrates the disposable Mayo instrument tray 24 having an edge 23, and exemplary contents, such as tubing 150, a cystoscopy irrigation set 152, an additional small drape 154 and a box of instruments 156. The contents of the tray are selected to be appropriate to specific procedures. In such embodiments, the selected contents are appropriate for an office-based hysteroscopy procedure. In such embodiments, suitable contents of the Mayo surgical tray stand drape 100 can include the disposable Mayo tray 24, gauze pads, surgical lubricant; disinfectant iodine solution, spinal and hypodermic needles, a cystoscopy irrigation set 152 with inflow and outflow tubing, surgical gloves, a disposable speculum and a drape 154.

FIG. 8B is a perspective view of an embodiment of the everted Mayo surgical tray stand drape 100 with the internal surfaces of the bottom 104, and sides 110, 114, now visible, as are side junctions 120, 122, and 124, and basal junctions 130, 132, 134 and 136. In preferred embodiments, instrument pockets 140 and a waste receptacle 144 are affixed to one or more sides. The instrument pockets 140 are the same or different sizes, with at least one pocket 140 of suitable dimensions to accommodate an endoscope. The hem 128 and the draw tape 138 are at the bottom edge of the everted Mayo surgical tray stand drape 100. The openings of the instrument pockets 140 and the waste receptacle 144 are at the end opposite to the hem 128.

Figure 9:
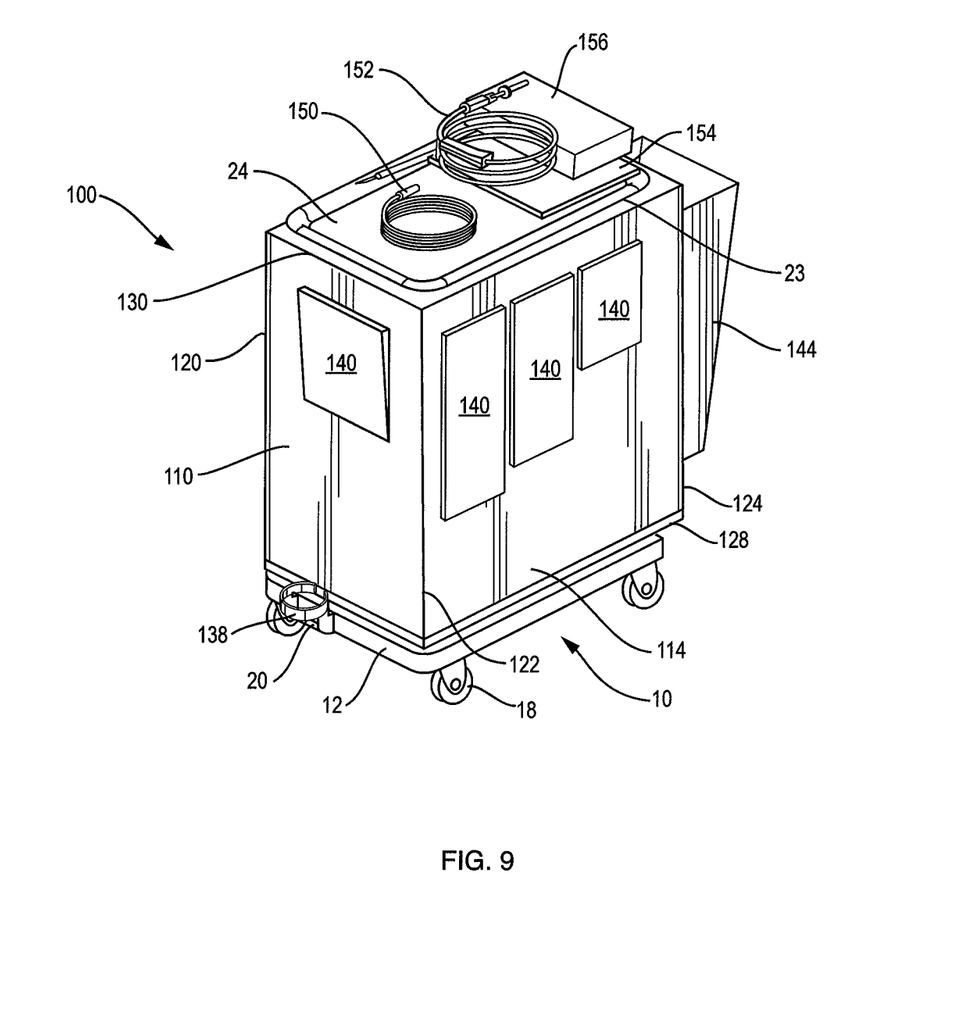
FIG. 9 is a perspective view of an embodiment of an instrument tray and an embodiment of the present Mayo surgical tray stand drape 100 showing the Mayo surgical tray stand drape everted for use and in place on a Mayo surgical tray stand 10.

FIG. 9 is a perspective view of the Mayo surgical tray stand drape 100 ready for use in place on the Mayo surgical tray stand 10, showing the base 12, the vertical support member 20, and the casters 18. The internal surface of sides 110 and 114 are visible, as are the lateral junctions 120, 122 and 124, the instrument pockets 140, the waste receptacle 144, a disposable Mayo instrument tray 24 with edge 23, a coil of tubing 150, a cystoscopy irrigation set 152, a small flat drape 154 and a box containing surgical instruments and consumable supplies 156. The hem 128 of the Mayo surgical tray stand drape 100 is positioned to maintain the desirable mobility of the Mayo surgical tray stand 10 by leaving the casters 18 unobstructed.

Figure 10:
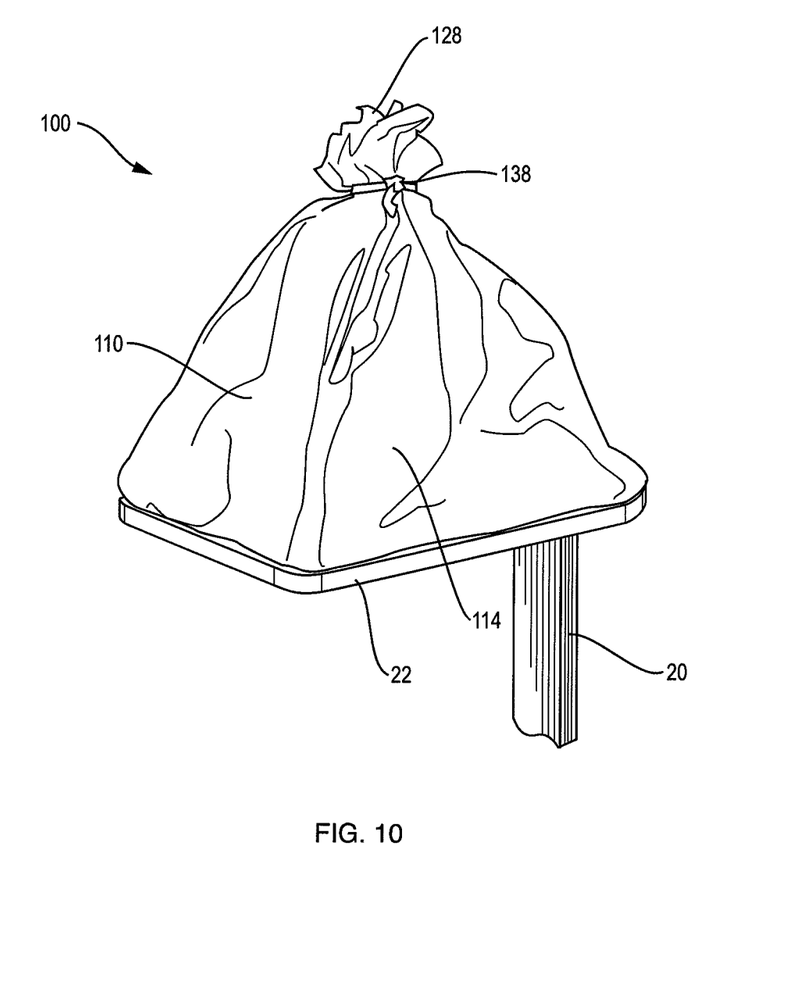
FIG. 10 is a perspective view of an embodiment of the present Mayo surgical tray stand drape 100 showing the Mayo stand drape closed and secured for disposal.

After the procedure has been completed, the hem 128 of the Mayo surgical tray stand drape 100 is raised to enclose the disposable Mayo instrument tray, the disposable surgical instruments and disposable waste. FIG. 10 is a perspective view of the Mayo stand cover 100 after use, showing the outer surface of sides 110 and 114, the horizontal generally rectangular support ring 22 and a portion of the vertical support member 20. The opening of the Mayo surgical tray stand drape 100 is closed using the draw tape 138 and secured by tying the draw tape 138 to secure the opening of the Mayo stand drape 100. In other embodiments, other or additional closure devices known in the art that are suitable for use with medical waste containers can be used, including, but not limited to, a tie cord, e.g., U.S. Pat. No. 5,040,904 (Cornwell), a self-adhesive tie, e.g., U.S. Pat. No. 5,286,111 (Brembilla) or clamping closure devices, e.g., U.S. Pat. No. 4,465,486 (Hill).

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

Unless otherwise defined, all technical and scientific terms used herein have the same meaning as commonly understood by one of ordinary skill in the art to which this invention belongs. All listed patents, patent publications and non-patent literature are incorporated herein by reference. In the case of inconsistencies, the present disclosure, including definitions, will control.

What is claimed is:

1. A convertible Mayo surgical tray stand drape comprising:
   a surgical instrument tray for fitting on a Mayo surgical tray stand;
   a bottom panel having an inner surface and an outer surface, the bottom panel having a length and width slightly larger than a length and width of the surgical instrument tray on the inner surface of the bottom panel;
   four sides having an inner surface and an outer surface, each of the four sides respectively attached at one corresponding edge to an edge of the bottom panel to form a basal junction and as packaged, and each of the four sides being attached to the adjacent sides to form four lateral junctions, gathered into folds to form a package wrapping the surgical instrument tray, wherein the folds are on the side of the package opposite the inner surface of the bottom panel and the package exposing the outer surface of each of the four sides; as unfolded, the four sides disposed substantially perpendicular to the bottom panel exposing the surgical instrument tray and the inner surfaces of the four sides, wherein the bottom panel and the attached four sides define an enclosed space having an opening, opposite to the outer surface of the bottom panel; and as reverted, the four sides being reverted exposing the outer surfaces of the four sides and the bottom panel;

a hem formed by first edges of the four sides opposite the bottom panel; and at least one closure device provided with the hem to close the opening, wherein, as reverted, the opening of the partially enclosed space is dosed by the at least one closure device.

2. The drape of claim 1 further comprising consumable supplies and instruments which are displaced on the surgical instrument tray which is covered before reverted and supported after reverted by the bottom panel.

3. The drape of claim 2 wherein the surgical instrument tray is affixed to the inner surface of the bottom panel.

4. The drape of claim 2 wherein the surgical instrument tray, consumable supplies and instruments are disposable.

5. The drape of claim 1 wherein the closure device is a draw tape, a tie cord, a self-adhesive tie, or a clamping closure device.

6. The drape of claim 1 wherein the bottom panel and the attached four sides are constructed of sterilizable flexible material having a substantially liquid-impermeable layer.

7. The drape of claim 1 further comprising at least one pocket affixed to the inner surface of one of the four sides.

8. The drape of claim 1 further comprising at least one waste receptacle affixed to the inner surface of the four sides.

9. A convertible Mayo stand drape comprising:

a surgical instrument tray for fitting on a Mayo surgical tray stand;

a bottom panel having an inner surface and an outer surface, the bottom panel having a length and width slightly larger than a length and width of the surgical instrument tray on the inner surface of the bottom panel;

four side panels, each having an inner surface and an outer surface, constructed of a sterilizable flexible material having a substantially liquid-impermeable layer, wherein each side panel is attached at one corresponding edge to an edge of the bottom panel to form a basal junction, and attached to the adjacent side panels on the edges adjacent to the basal junction to form four lateral junctions; as packaged, the four side panels gathered into folds to form a package wrapping the surgical instrument tray, wherein the folds are on the side of the package opposite the inner surface of the bottom panel and the package exposing the outer surface of each of the four sides; as unfolded, the four sides disposed substantially perpendicular to the bottom panel exposing the surgical instrument tray and the inner surfaces of the four sides, wherein the bottom panel and the attached four sides define an enclosed space having an opening, opposite to the outer surface of the bottom panel; and as reverted, the four sides being reverted exposing the outer surfaces of the four sides and the bottom panel;

a hem formed by edges of the four side panels opposite the bottom panel; and at least one closure device provided with the hem to close the opening, wherein, as reverted, the opening of the enclosed space is closed by the at least one closure device.

10. The drape of claim 9 further comprising consumable supplies and instruments which are displaced on the surgical instrument tray covered before reverted and supported after reverted by the bottom panel.

11. The drape of claim 10 wherein the surgical instrument tray is affixed to the inner surface of the bottom panel.

12. The drape of claim 9 further comprising at least one pocket affixed to the inner surface of one side panel.

13. The drape of claim 9 further comprising one waste receptacle affixed to the inner surface of one side panel.

14. The drape of claim 9 wherein the closure device is a draw tape, a tie cord, a self-adhesive tie, or a clamping closure device.

15. A convertible disposable drape thr a surgical instrument stand comprising:

a surgical instrument tray for fitting on a Mayo surgical tray stand wherein said Mayo surgical tray stand includes a support ring;

an elongated enclosure, having an inner surface and an outer surface, made of a sterilizable flexible material having a substantially liquid-impermeable layer, the elongated enclosure having an open end and a closed end formed by a panel dimensioned to be about the size and shape of the surgical instrument tray; as packaged, the elongated enclosure gathered into a package wrapping the surgical instrument tray and exposing the outer surface; as unfolded, the panel perpendicular to the longitudinal axis of the elongated enclosure exposing the surgical instrument tray and the inner surface; and as reverted, the elongated enclosure being reverted exposing the outer surface;

a hem formed by edges of the open end of the elongated enclosure, wherein, as unfolded, the distance between the hem of the open end and the basal junction of the closed end being less than the distance from the support ring of the Mayo surgical stand to the floor; and at least one closure device provided with the hem to close the open end, wherein, as reverted, the open end of the elongated enclosure is closed by the at least one closure device.

16. The drape of claim 15 further comprising consumable supplies and instruments.

17. The drape of claim 16 wherein the surgical instrument tray is affixed to the inner surface of the panel.

18. The drape of claim 15 wherein the closure device is a draw tape, a tie cord, a self-adhesive tie, or a clamping closure device.

* * * * *